(12) United States Patent
Meyer et al.

(10) Patent No.: US 6,559,307 B2
(45) Date of Patent: May 6, 2003

(54) PROCESS FOR THE PREPARATION OF SUBSTITUTED PYRIMIDINES

(75) Inventors: Oliver Meyer, Ingelheim (DE); Dieter Gutheil, Bad Kreuznach (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/896,078

(22) Filed: Jun. 29, 2001

(65) Prior Publication Data

US 2002/0004600 A1 Jan. 10, 2002

Related U.S. Application Data

(62) Division of application No. 09/547,666, filed on Apr. 12, 2000, now Pat. No. 6,281,358.
(60) Provisional application No. 60/129,462, filed on Apr. 15, 1999, and provisional application No. 60/139,356, filed on Jun. 15, 1999.

(51) Int. Cl.[7] .............................................. C07D 239/34
(52) U.S. Cl. ...................................... 544/319; 544/295
(58) Field of Search ................................. 544/319, 295

(56) References Cited

U.S. PATENT DOCUMENTS

| | | | |
|---|---|---|---|
| 3,498,984 A | 3/1970 | Santilli et al. ........... 260/256.5 |
| 4,824,949 A | 4/1989 | Lachhein et al. ........... 544/320 |
| 4,831,138 A | 5/1989 | Lachhein .................... 544/320 |
| 4,831,139 A | 5/1989 | O'Murchu .................. 544/323 |
| 5,824,624 A | 10/1998 | Kleeman et al. ............ 504/242 |
| 5,840,892 A | 11/1998 | Bessard et al. ............. 544/302 |
| 5,849,758 A | 12/1998 | Kleeman et al. ............ 514/269 |

FOREIGN PATENT DOCUMENTS

| | | |
|---|---|---|
| WO | WO 90/06918 | 6/1990 |
| WO | WO 98/30549 | 7/1998 |
| WO | WO 98/40379 | 9/1998 |
| WO | WO 98/56789 | 12/1998 |

OTHER PUBLICATIONS

J. Medwid et al., "Preparation of Triazolo [1,5–c] pyridines as Potential Dichlorides and Antiasthma Agents", J. Med. Chem. 1990 33, 1230–1241.

W. Schroth et al., "Synthesis of 1,3–thiazine–6–thiones From Formylketene Dichlorides and Thioamides", Z. Chem. 24 (1984), 435–436.

Chemical Abstracts, 103 : 6290 (1985).

*Primary Examiner*—John M. Ford
(74) *Attorney, Agent, or Firm*—Keil & Weinkauf

(57) ABSTRACT

The invention relates to a process for the preparation of substituted pyrimidines of formula I,

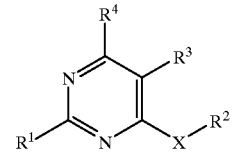

(I)

wherein
$R^1$, $R^2$, $R^3$, $R^4$ and X are as defined in claim 1,
which comprises reacting an amidine of formula II,

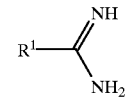

(II)

or a salt thereof, with a 3,3-disubstituted vinylcarbonyl compound of formula III

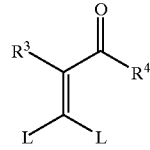

(III)

wherein L represent a halogen atom or a group of formula —X—$R^2$, (a) in an inert solvent, in the presence of a base and a compound of formula IV

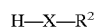

(IV)

in the event that L represent a halogen atom, or (b) in an inert solvent and in the presence of a base, in the event that L represents a group of formula —X—$R^2$.

2 Claims, No Drawings

PROCESS FOR THE PREPARATION OF SUBSTITUTED PYRIMIDINES

This application is a division of application Ser. No. 09/547,666 filed Apr. 12, 2000, now U.S. Pat. No. 6,281,358, which claims the benefit of Provisional application Ser. No. 60/129,462, Apr. 15, 1999, and claims the benefit of Provisional application Ser. No. 60/139,356, filed Jun. 15, 1999.

BACKGROUND OF THE INVENTION

The present invention relates to an improved process for the preparation of substituted pyrimidines.

Pyrimidines, which are substituted in the 4-position by a hydrocarbyloxy or hydrocarbylthio group are of great commercial interest as highly effective pesticides or pharmaceuticals. U.S. Pat. No. 3,498,984 discloses 2-phenyl-4-thiopyrimidines with interesting pharmaceutical properties. U.S. Pat. No. 5,824,624 describes herbicidal compositions comprising 2-phenyl-4-oxypyrimidines. The International Patent Applications WO 98/40379 and WO 98/56789 disclose herbicidal 4-oxypyrimidines, in which a 5-membered heteroaromatic group is attached to the 2-position position of the pyrimidine moiety.

These compounds can be prepared for example in a multi-step process including the steps of treating a benzamidine hydrochloride with a substituted acetylacetate in the presence of a strong base to form a 2-phenylpyrimid-4-one, which is subsequently treated with a halogenating agent, in particular a phosphoryl halide to yield a 4-halo-2-phenylpyrimidine, which is reacted with an alcohol or a thioalcohol.

However, this process cannot be used for manufacture of relatively large quantities on an industrial scale due to the high risk of uncontrollable heat generation during the aqueous work up of the halogenation step.

W. Schroth et al., disclose the preparation of 1,3-thiazin-6-thiones by condensation of 3,3-dichloroacrolein and thioamides in the presence of trifluoroborane.

However, there is no motivation to apply this reaction on the manufacture of substituted pyrimidines, especially, since trifluoroborane is not applicable in large scale productions.

SUMMARY OF THE INVENTION

The present invention provides an effective and efficient process for the preparation of substituted pyrimidines of formula I,

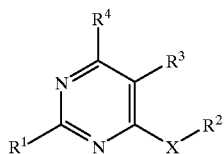

(I)

wherein
$R^1$ and $R^2$ each independently represent an optionally substituted alkyl, cycloalkyl, phenyl or heteroaryl group,
$R^3$ and $R^4$ each independently represent a hydrogen atom or an optionally substituted alkyl or phenyl group, and
X represents O or S.

which comprises
reacting an amidine of formula II,

(II)

or a salt thereof, wherein $R^1$ has the meaning given for formula I, with a 3,3-disubstituted vinylcarbonyl compound of formula III

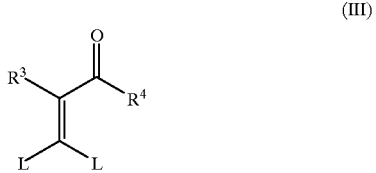

(III)

wherein $R^3$ and $R^4$ have the meaning given, and
L represent a halogen atom or a group of formula —X—$R^2$,
(a) in an inert solvent, in the presence of a base and a compound of formula IV

H—X—$R^2$ (IV)

wherein X and $R^2$ have the meaning given, in the event that L represent a halogen atom, or
(b) in an inert solvent and in the presence of a base, in the event that L represents a group of formula —X—$R^2$.

It is, therefore, an object of the present invention to provide an efficient new process for the preparation of substituted pyrimidines.

Other objects and advantages of the present invention will be apparent to those skilled in the art from the following description and the appended claims.

DETAILED DESCRIPTION OF THE PREFERRED EMBODIMENTS

When any groups are designated as being optionally substituted, the substituent groups which are optionally present may be any of those customarily employed in the modification and/or development of pesticidal/pharmaceutical compounds and are especially substituents that maintain or enhance the herbicidal activity associated with the compounds of the present invention, or influence persistence of action, soil or plant penetration, or any other desirable property of such herbicidal compounds. There may be one or more of the same or different substituents present in each part of the molecules.

In relation to moieties defined above as comprising an optionally substituted alkyl or cycloalkyl group, specific examples of such substituents include phenyl, halogen atoms, nitro, cyano, hydroxyl, $C_{1-4}$-alkoxy, $C_{1-4}$-haloalkoxy and $C_{1-4}$-alkoxycarbonyl groups.

In relation to moieties defined above as comprising an optionally substituted phenyl group or heteroaryl group, optional substituents include halogen, especially fluorine, chlorine and bromine atoms, and nitro, cyano, amino, hydroxyl, $C_{1-4}$-alkyl, $C_{1-4}$-alkoxy, $C_{1-4}$-haloalkyl, $C_{1-4}$-haloalkoxy, $C_{1-4}$-haloalkylthio and halosulfanyl groups such as $SF_5$. 1 to 5 substituents may suitably be employed, 1 to 2 substituents being preferred. Typically haloalkyl, haloalkoxy and haloalkylthio groups are trifluoromethyl, trifluoromethoxy, difluoromethoxy and trifluoromethylthio groups.

In general terms, unless otherwise stated herein, the term alkyl as used herein with respect to a radical or moiety refer to a straight or branched chain radical or moiety. As a rule, such radicals have up to 10, in particular up to 6 carbon atoms. Suitably an alkyl moiety has from 1 to 6 carbon atoms, preferably from 1 to 3 carbon atoms. A preferred alkyl moiety is the methyl or especially the ethyl group.

In general terms, unless otherwise stated herein, the term cycloalkyl as used herein with respect to a radical or moiety refers to a cycloalkyl radical which has up to 10, in particular up to 8 carbon atoms. Suitably a cycloalkyl moiety has from 3 to 6 carbon atoms, preferably from 3 or 6 carbon atoms. A preferred cycloalkyl moiety is the cyclopropyl, cyclopentyl and the cyclohexyl group.

In general terms, unless otherwise stated herein, the term heteroaryl as used herein with respect to a radical or moiety refers to a nitrogen containing 5- or 6-membered heteroaromatic radical or moiety. As a rule, such radicals exhibit at least one nitrogen atom and in the case of the five-membered radicals optionally one oxygen or sulfur atom; they are preferably selected from the 5-membered azoles, diazoles, triazoles, thiazoles, isothiazoles, thiadiazoles, in particular pyrrole and pyrazole and the 6-membered azines and diazines, in particular pyridine, pyrimidine, pyridazine and pyrazine.

In a preferred embodiment $R^1$ represents an optionally substituted phenyl, pyrid-3-yl, pyridazine-2-yl, pyrazine-3-yl, thiazol2-yl, oxazol-2-yl, 1,3,4-thiadiazol-2-y, 1,2,4-oxadiazol-2-yl, 1,3,4-oxadiazol-2-yl, pyrazol-1-yl or $C_{3-6}$ cycloalkyl group.

In a preferred embodiment $R^2$ represents an optionally substituted phenyl, pyrid-2-yl, pyrid-3-yl, pyrid-4yl, pyrazol-5-yl, pyridazine-2-yl or $C_{3-6}$ cycloalkyl group.

The groups $R^1$ and $R^2$ each independently are preferable substituted by one or more alkyl, fluoroalky, alkoxy or fluoroalkoxy group.

Suitable bases are weak organic or inorganic bases, preferably alkali hydrogencarbonates, such as sodium hydrogencarbonate, alkali carbonates, such as potassium carbonate or sodium carbonate, and tertiary amines, such as pyridine or triethylamine.

Further preferred embodiments of the process according to the present invention are a processes wherein:

the reaction is carried out in the presence of a base selected from the group consisting of, alkali carbonates and tertiary amines, in particular potassium carbonate or sodium carbonate;

the amidine of formula II to 3,3-disubstituted vinylcarbonyl compound of formula III molar ratio is from 1:5 to 1:0.5, in particular from 1:1.5 to 1:0.7, most preferred from 1:1.1 to 1:0.9;

the reaction step further comprises stirring a mixture consisting essentially of the amidine of formula II, the 3,3-disubstituted vinylcarbonyl compound of formula III, an inert diluent, a base and an optionally substituted alcohol, thioalcohol, phenol or thiophenol at a temperature from 0° C. to 150° C., preferably from 60° C. to 145° C., in particular from 80° C. to 140° C., most preferred at about the boiling point of the diluent;

the inert diluent is selected from the group consisting of acetonitril, benzene, toluene, xylene, hexane, cyclohexane, dichloromethane, tetrachloromethane, diethylether, diisopropylether, tert-butylmethylether, 2,2-dimethoxypropane, dimethoxyethane, diethoxyethane, tetrahydrofuran, tetrahydropyran, dimethylformamide, dimethylacetamide, N-methylpyrrolidone, dimethylsulfoxide and dioxane, and a mixture thereof, in particular toluene, dimethoxyethane or acetonitril;

$R^1$ represents a phenyl group which is substituted by at least one halogen atom, or at least one alkyl, alkoxy, haloalkyl or haloalkoxy group, in particular a phenyl group which is substituted by one or two chlorine or fluorine atoms, or one or two $C_{1-4}$ alkyl, $C_{1-4}$ alkoxy, $C_{1-4}$ fluoroalkyl or $C_{1-4}$ fluoroalkoxy groups, $R^1$ is most preferably a 4-trifluoromethylphenyl, difluoromethoxypyrid-2-yl or 1-methyl-3-triflouromethylpyrazol 1-methyl-3-trifluoromethylpyrazol-5-yl group;

$R^1$ and $R^2$ each independently represent a phenyl group which is substituted by at least one halogen atom, and/or at least one alkyl, alkoxy, haloalkyl or haloalkoxy group, X represents O, and which comprises that the reaction step is carried out in the presence of a phenol, which is substituted by at least one halogen atom, and/or at least one alkyl, alkoxy, haloalkyl or haloalkoxy group, in particular a phenol which is substituted by one or two chlorine or fluorine atoms, or one or two $C_{1-4}$ alkyl, $C_{1-4}$ alkoxy, $C_{1-4}$ fluoroalkyl or $C_{1-4}$ fluoroalkoxy groups, most preferred a 3-trifluoromethylphenol;

wherein the 3,3-disubstituted vinylcarbonyl compound of formula III is 3,3-dichloroacrolein.

The compounds of formula II or the salts thereof are preferably optionally substituted benzamidines or benzamidinum salts, most preferred 4-trifluoromethylbenzamidine, which can be prepared from commercially available optionally substituted benzonitriles, in particular 4-trifluoromethylbenzonitril, by addition of ammonia or ammonium salts.

Preferred benzamidinium salts are chlorides, sulfates, nitrates and carboxylates, in particular acetates and thioglycolates.

The 3,3-disubstituted vinylcarbonyl of formula III, wherein L represents a halogen atom are commercially available or can be prepared by reaction of tetrahalometharies with vinylethers.

In a preferred embodiment of this invention, the 1,1,1,3-tetrahalo-3-alkoxypropane obtained in this reaction can be hydrolysed in-situ to obtain the corresponding vinylcarbonyl compound of formula III, which is subsequently reacted, preferably without further isolation and/or purification steps, i.e., in a one-pot-synthesis, with the compound of formual II.

The 3,3-disubstituted vinylcarbonyl of formula III, wherein L represents a group of formula —X—$R^{2,}$ can be prepared by reaction of a compound of formula III, wherein L represents a halogen atom with a compound of formula IV

H—X—$R^2$ (IV)

optionally in the presence of a base.

As a rule the reaction between the amidine of formula II, the 3,3-disubstituted vinyl carbonyl compound of formula III and optionally the alcohol, phenol, thioalcohol or thiophenol is carried out at elevated temperatures, preferably between 35° C. and 150° C., in particular between 80° C. and 145° C., most preferred at boiling point of the diluent.

The crude product obtained can be purified according to standard methods for example by distillation in vacuo, chromatographic methods or crystallization.

The reaction is as a rule completed within 5 to 50 hours, in particular 10 to 25 hours.

In a particularly preferred embodiment of the process according to this invention 3,3-dichloroacrolein (1 mole) optionally diluted with an inert diluent, in particular acetonitril, is added to a mixture consisting of a benzamidine of formula II, wherein $R^1$ is a an optionally substituted phenyl group, in particular 4-trifluoromethylbenzamidine (1 mole), an optionally substituted phenol, in particular 3-trifluoromethylphenol (1.1 moles), potassium carbonate (3 to 5 moles) and a diluent, which is stirred under reflux. The reaction mixture is stirred for 10 to 40 hours under reflux. The reaction mixture is stirred for 10 to 40 hours under reflux and subsequently cooled down to ambient temperature, and filtered. The organic phase is concentrated in vacuo. The residue is washed with an organic solvent and the solvent is distilled off. The residue is purified by chromatography.

The compounds of formula 1 obtainable according to the process according this invention are partly known and partly novel. The invention relates also to the novel compounds of formula 1A,

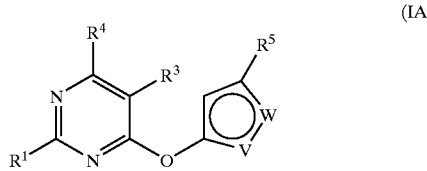

(IA)

wherein $R^3$ and $R^4$ have the meaning given for formula 1, and $R^1$ represents an optionally substituted $C_{3-8}$ cycloalkyl or pyrazin-2-yl group. $R^5$ represents a halogen atom or a haloalkyl or haloalkoxy group, and W—V represents N—CH, S—CH, N—CH—CH, CH—CH—CH or N—N ($R^6$), in which $R^6$ represents a $C_{1-4}$ alkyl group.

In order to facilitate a further understanding of the invention, the following illustrative examples are presented. The invention is not limited to the specific embodiments described or illustrated, but encompasses the full scope of the appended claims.

EXAMPLE 1

Preparation of 4-(3-Triflouromethylphenoxy)-2-(4-Triflouromethylphenyl)-Pyrimidine 3,3-Dichloroacrolein (10 mmoles) diluted with acetonitril (50 ml), is slowly added to a mixture consisting of a 4-trifluoromethylbenzamidine (10 mmoles), 3-trifluoromethylphenol (11 mmoles), potassium carbonate (40 mmoles) and acetonitril (100 ml), which is stirred under reflux. When the addition of 3,3-dichloroacrolein is completed additional 4-trifluoromethylbenzamidine (0.5 mmoles) is added. The reaction mixture is stirred for 20 hours under reflux and subsequently cooled down to ambient temperature and filtered through silica. The organic phase is washed with ethyl acetate and concentrated in vacuo. The residue purified by chromatography on $Al_2O_3$ (petrol ethers/ethyl acetate: 2/1) to yield 3.25 g (85%) of the pure product having a melting point of 66–67° C.

Analogously are prepared 3-methyl-4-(3-trifluoromethylphenoxy)-2-(4-trifluoromethylphenyl)-pyrimidine, 5-4-(3-trifluoromethylphenoxy)-2-(4-trifluoromethylphenyl)-pyrimidine, 4-phenoxy-2-(4-trifluoromethylphenyl)pyrimidine

EXAMPLES 2 TO 8

Preparation of 4-(3-Trifluoromethylphenoxy)-2-(4-Trifluoromethylphenyl)-Pyrimidine, Analogously to example 1 4-trifluoromethylbenzamidine or the salts thereof are reacted with 3,3-dichloroacrolein in the presence of 3-trifluoromethylphenol in different solvents at different temperatures The reactants and solvents, the reaction temperature and yields are shown in table 1 in which the following abbreviations have been used:

| TFBA | 4-trifluoromethylbenzamidine |
| TFBA * HCl | 4-trifluoromethylbenzamidine hydrochloride |
| TFBA * Ac | 4-trifluoromethylbenzamidinium acetate |
| TFBA * TG | 4-trifluoromethylbenzamidinium thioglycolate |
| TBME | tert-butylmethylether |
| DME | dimethoxyethane |

TABLE I

Examples 2 to 8

| Example | starting material | solvent | temperature | Yield (%) |
|---|---|---|---|---|
| 2 | TFBA | acetonitril | reflux | 85 |
| 3 | TFBA | DME | reflux | 85 |
| 4 | TFBA | toluene | 90° C. | 72 |
| 5 | TFBA | TBME | reflux | 39 |
| 6 | TFBA * HCl | DME | reflux | 84 |
| 7 | TFBA * Ac | DME | reflux | 81 |
| 8 | TFBA * TG | DME | reflux | 47 |

EXAMPLE 9

Preparation of 4-(3-Trifluoromethylphenoxy)-2-(4-Trifluoromethylphenyl)-Pyrimidine A mixture of 3,3-bis-(3-trifluoromethylphenoxy)-acrolein (10 mmoles), 4-trifluoromethylbenzamidine (10 mmoles), potassium carbonate (10 mmoles) and acetonitril (100 ml), is stirred at 80° C. for four hours. The reaction mixture is cooled down to ambient temperature and filtered through silica. The organic phase is washed with ethyl acetate and concentrated in vacuo. The residue is purified by chromatography on $Al_2O_3$ (petrol ethers/ethyl acetate: 2/1) to yield 3.06 g (80%) of the pure product having a melting point of 66° C.

EXAMPLE 10

Preparation of 4-(3-Trifluoromethylphenoxy)-2-(4-Trifluoromethylphenyl)-Pyrimidine 3-Trifluoromethylphenol (5 mmoles) and subsequently 3,3-dichloroacrolein (5 mmoles) are added to a mixture consisting of a 4-trifluoromethylbenzamidinium acetate (5 mmoles), sodium carbonate (40 mmoles) and acetonitril (35 ml), which is stirred under reilux. The reaction mixture is stirred for 20 hours under reflux and subsequently cooled down to ambient temperature and filtered through silica. The organic phase is washed with ethyl acetate and concentrated in vacuo. The residue is purified by chromatography on $Al_2O_3$ (petrol ethers/ethyl acetate: 2/1) to yield 1.1 g (60%) of the pure product having a melting point of 66–67° C.

EXAMPLE 11

Enhanced Preparation of 4-(3-Trifluoromethylphenoxy)-2-(4-Trifluoromethylphenyl)-Pyrimidine Water (20 mmoles) is added to a solution of 1,1,1,3-tetrachloro-3-ethoxypropane (10 mmoles) in dimethoxyethane (25 ml). The reaction mixture is stirred for 2 h under reflux. The resulting mixture is slowly added to a mixture consisting of a 4-trifluoromethylbenzamidine hydrochloride (10 mmoles), 3-trifluoromethylphenol (11 mmoles), potassium carbonate (60 mmoles) and dimethoxyethane (50 ml), which is stirred under reflux. When the addition of 3,3-dichloroacrolein solution is completed additional 4-trifluoromethylbenzamidine hydrochloride (1 mmoles) is added. The reaction mixture is stirred for 2 hours under reflux and subsequently cooled down to ambient temperature, filtered through silica, and the organic phase is concentrated in vacuo. The residue is purified by chromatography on $SiO_2$ (petrol ethers/diisopropylether: 6/1) to yield 3,07 g (80%) of the product having a melting point of 66–67° C.

EXAMPLE 12

Preparation of 2-(4-Chlorophenyl)-4-(3-Trifluoromethylphenoxy)Pyrimidine 3,3-Dichloroacrolein (10 mmoles) diluted with dimethoxyethane (35 ml), is slowly added to a mixture consisting of a 4-chlorobenzamidine hydrochloride (10 mmoles), 3-trifluoromethylphenol (11 mmoles), potassium carbonate (40 mmoles) and dimethoxyethane (40 ml), which is stirred under reflux. When the addition of 3,3-dichloroacrolein is completed additional 4-chlorobenzamidine hydrochloride (1 mmoles) is added. The reaction mixture is stirred for 3 hours under reflux and subsequently cooled down to ambient temperature over night and filtered through silica. The organic phase is concentrated in vacuo. The residue was purified by chromatography on $Al_2O_3$ (petrol ethers/ethyl acetate: 20/1) to yield 2.79 g (80%) of the pure product having a melting point of 92° C.

EXAMPLE 13

Preparation of 4-(3-Trifluoromethylphenoxy)-2-(4-Fluorophenyl) Pyrimidine 3,3-Dichloroacrolein (10 mmoles) diluted with dimethoxyethane (35 ml), is slowly added to a mixture consisting of a 4-fluorobenzamidine acetate (10 mmoles), 3-trifluoromethylphenol (11 mmoles), potassium carbonate (40 mmoles) nd dimethoxyethane (40 ml), which is stirred under reflux. When the addition of 3,3-dichloroacrolein is completed additional 4-fluorobenzamidine acetate (1 mmoles) is added. The reaction mixture is stirred for 3 hours under reflux and subsequently cooled down to ambient temperature over night and filtered through silica. The organic phase is concentrated in vacuo. The residue was purified by chromatography on $Al_2O_3$ (petrol ethers/ethyl acetate: 20/1) to yield 2.52 g (75%) of the pure product having a melting point of 52° C.

EXAMPLE 14

Preparation of 2-Cyclopropyl-4-(3-Trifluoromethylphenoxy) Pyrimidine 3,3-Dichloroacrolein (10 mmoles) diluted with dimethoxyethane (35 ml), is slowly added to a mixture consisting of a cyclopropylcarbamidine hydrochloride (10 mmoles), 3-trifluoromethylphenol (11 mmoles), potassium carbonate (40 rnmoles) and dimethyoxyethane (40 ml), which is stirred under reflux. When the addition of 3,3-dichloroacrolein is completed additional cyclopropylcarbamidine hydrochloride (1 mmoles) is added. The reaction mixture is stirred for 3 hours under reflux and subsequently cooled down to ambient temperature over night and filtered through silica. The organic phase is concentrated in vacuo. The residue was purified by chromatography on $Al_2O_3$ (petrol ethers/ethyl acetate: 20/1) to yield 2.1 g (75%) of the pure product having as a colorless liquid; $^1H$ NMR ($CDCl_3$); δ=2.10 ppm (m, N=C(=N)=CH).

EXAMPLE 15

Preparation of 2-(4-Flourophenyl)-4-(5-Trifluoromethyl2-Methylpyrazol-3-Yloxy) Pyrimidine Water (20 mmoles) is added to a solution of 1,1,1,3-tetrachloro-3-ethoxypropane (10 mmoles) in dimethoxyethane (25 ml). The reaction mixture is stirred for 6½ h at 40° C. The resulting mixture is slowly added to a mixture consisting of 4-fluorobenzamidine hydrochloride (10 mmoles), 4-trifluoromethyl-2-methylpyrazol-1-on (11 mmoles), potassium carbonate (60 mmoles) and dimethoxyethane (50 ml), which is stirred under reflux. When the addition of 3,3-dichloroacrolein solution is completed additional 4-fluorobenzamidine hydrochloride (0.5 mmoles) is added. The reaction mixture is stirred for 2 hours under reflux and subsequently cooled down to ambient temperature. filtered through a silica, and the organic phase is concentrated in vacuo. The residue is purified by chromatography on $SiO_2$ (petrol ethers/ethylacetate: 2/1) to yield 1.40 g (46%) of beige crystals having a melting point of 101–102° C.

EXAMPLE 16

Preparation of 4-(2-Difluoromethoxypyridin-4-Yloxy)-2-(Pyrazin-2-yl)-Pyrimidine Water (20 mmoles) is added to a solution of 1,1,1,3-tetrachloro-3-ethoxypropane (10 mmoles) in dimethoxyethane (25 ml). The mixture is stirred for 2 h at 60° C. The resulting mixture is slowly added to a mixture consisting of a pyrazine-2-carboxamidine hydrochloride (10 mmoles). 2-difluoromethoxypyridin-4-ol (10 mmoles), potassium carbonate (60 mmoles) and dimethoxyethane (50 ml), which is stirred under reflux. When the addition of 3,3-dichloroacrolein solution is completed additional pyrazine-2-carboxamidine hydrochloride (0.5 mmoles) is added. The reaction mixture is stirred for 2 hours under reflux and subsequently cooled down to ambient temperature, filtered through silica, and the organic phase is concentrated in vacuo. The residue is purified by chromatograph on $SiO_2$ (ethyl acetate) to yield 2,60 g (82%) of beige crystals having a melting point of 128–129° C.

EXAMPLE 17

Preparation of 4-(3-Trifluoromethylphenoxy)-2-(3,5-Dimethylpyrazol1-yl-Pyrimidine Water (20 mmoles) is added to a solution of 1,1,1,3-tetrachloro-3-ethoxypropane (10 mmoles) in dimethoxyethane (25 ml). The mixture is stirred for 2 h at 90° C. The resulting mixture is slowly added to a mixture consisting of a 3,5-dimethylpyrazole-1-carboxamidine nitrate (10 mmoles), 3-trifluoromethylphenol (10 mmoles), potassium carbonate (60 mmoles) and dimethoxyethane (50 ml), which is stirred under reflux. When the addition of 3,3-dichloroacrolein solution is completed additional 3,5-dimethylpyrazole-1-carboxamidine nitrate (0.5 mmoles) is added. The reaction mixture is stirred for 10 hours under reflux and subsequently cooled down to ambient temperature, filtered through silica, and the organic phase is concentrated in vacuo. The residue is purified by chromatography on SiO$_2$ (ethyl acetate) to give 2,2 g of a yellow solid. The solid was washed with petrol ether (50 ml) to yield 1,75 g (52%) of coloroless crystals having a melting point of 101–102° C.

What is claimed is:

1. A process for the preparation of substituted pyrimidines of formula IA

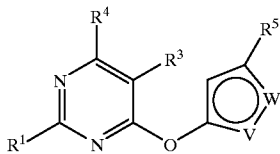
(IA)

wherein
- $R^3$ and $R^4$ each independently represent a hydrogen atom, alkyl optionally substituted by phenyl, halogen, nitro, cyano, hydroxyl, $C_{1-4}$-alkoxy, $C_{1-4}$-haloalkoxy or $C_{1-4}$-alkoxycarbonyl, or represents phenyl optionally substituted by halogen, nitro, cyano, hydroxyl, $C_{1-4}$-alkyl, $C_{1-4}$alkoxy, $C_{1-4}$-haloalkyl, $C_{1-4}$-haloalkoxy $C_{1-4}$-haloalkylthio or halosulfanyl, and
- $R^1$ represents $C_{3-8}$ cycloalkyl optionally substituted by phenyl, halogen, nitro, cyano, amino, hydroxyl, $C_{1-4}$-alkoxy, $C_{1-4}$-haloalkoxy or $C_{1-4}$-alkoxycarbonyl, or represents pyrazin-2-yl optionally substituted by halogen, nitro, cyano, amino, hydroxyl, $C_{1-4}$-alkyl, $C_{1-4}$-alkoxy, $C_{1-4}$-haloalkyl, $C_{1-4}$-haloalkoxy $C_{1-4}$-haloalkylthio or halosulfanyl,
- $R^5$ represent a halogen atom or a haloalkyl or haloalkoxy group and
- W-V represents N—CH, S—CH, N—CH—CH, CH—CH—CH or N—N($R^6$), in which $R^6$ represents a $C_{1-4}$ alkyl group which comprises reacting an amidine of formula II,

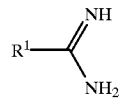
(II)

or a salt thereof with 3,3-dichloroacrolein in an inert solvent, in the presence of a base and in the presence of a compound of formula IV

(IV), wherein X denotes oxygen and $R^2$ represents a group

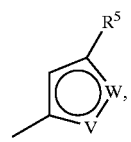

and which further comprises perparing the 3,3-dichloroacrolein by an in-situ hydrolysis of a 1,1,1,3-tetrachloro-3-alkoxypropane.

2. A compound of formula IA

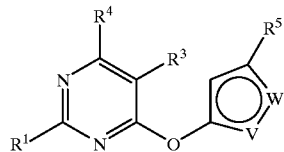
(IA)

wherein $R^3$ and $R^4$ each independently represent a hydrogen atom, alkyl optionally substituted by phenyl, halogen, nitro, cyano, hydroxyl, $C_{1-4}$-alkoxy, $C_{1-4}$-haloalkoxy or $C_{1-4}$-alkoxycarbonyl, or represent phenyl optionally substituted by halogen, nitro, cyano, amino, hydroxyl, $C_{1-4}$-alkyl, $C_{1-4}$-alkoxy, $C_{1-4}$-haloalkyl, $C_{1-4}$-haloalkoxy $C_{1-4}$-haloalkylthio or halosulfanyl, and $R^1$ represents $C_{3-8}$ cycloalkyl optionally substituted by phenyl, halogen, nitro, cyano, amino, hydroxyl, $C_{1-4}$-alkyl, $C_{1-4}$-alkoxy, $C_{1-4}$-haloalkoxy or $C_{1-4}$-alkoxycarbonyl, or represents pyrazin-2-yl optionally substituted by halogen, nitro, cyano, hydroxyl, $C_{1-4}$-alkyl, $C_{1-4}$-alkoxy, $C_{1-4}$-haloalkyl, $C_{1-4}$-haloalkoxy, $C_{1-4}$-haloalkylthio or halosulfanyl, $R^5$ represents a halogen atom or a haloalkyl or haloalkoxy group, and W-V represents N—CH, S—CH, N—CH—CH, CH—CH—CH or N—N($R^6$), in which $R^6$ represents a $C_{1-4}$ alkyl group.

* * * * *

UNITED STATES PATENT AND TRADEMARK OFFICE
CERTIFICATE OF CORRECTION

PATENT NO. : 6,559,307 B2
DATED : May 6, 2003
INVENTOR(S) : Oliver Meyer and Dieter Gutheil It is certified that error appears in the above-identified patent and that said Letters Patent is hereby corrected as shown below:

Column 9,
Line 24, after "cyano," insert -- amino, --;
Line 28, delete "amino,".

Column 10,
Line 38, delete "amino,";
Lines 38 and 39, delete "$C_{1-4}$-alkyl,";
Line 41, after "cyano," insert -- amino, --.

Signed and Sealed this

Second Day of September, 2003

JAMES E. ROGAN
*Director of the United States Patent and Trademark Office*